United States Patent [19]

Fischetti et al.

[11] Patent Number: 5,604,109
[45] Date of Patent: Feb. 18, 1997

[54] METHOD FOR EXPOSING GROUP A STREPTOCOCCAL ANTIGENS AND AN IMPROVED DIAGNOSTIC TEST FOR THE IDENTIFICATION OF GROUP A STREPTOCOCCI

[75] Inventors: Vincent A. Fischetti, West Hempstead, N.Y.; David Bernstein, Sykesville, Md.

[73] Assignee: New Horizons Diagnostics Corporation, Columbia, Md.

[21] Appl. No.: 305,800

[22] Filed: Sep. 13, 1994

Related U.S. Application Data

[63] Continuation of Ser. No. 919,616, Jul. 29, 1992, abandoned, which is a continuation of Ser. No. 916,800, Oct. 8, 1986, abandoned.

[51] Int. Cl.⁶ .................................................. G01N 33/569
[52] U.S. Cl. ...................... 435/7.34; 435/29; 435/30; 435/34; 435/36; 435/961; 435/962; 435/975; 436/518; 436/524; 436/531; 436/533; 436/536; 436/808
[58] Field of Search ............................ 436/518, 524, 436/531, 533, 536, 808; 435/7.1, 7.2, 7.34, 29, 30, 34, 36, 39, 810, 885, 961, 962, 975

[56] References Cited

U.S. PATENT DOCUMENTS

| | | | |
|---|---|---|---|
| 4,281,061 | 7/1981 | Zuk et al. | 436/537 X |
| 4,313,734 | 2/1982 | Leuvering | 436/525 |
| 4,618,576 | 10/1986 | Rosenstein et al. | 435/7 |
| 4,626,502 | 12/1986 | Krause-Hooyman | 435/7 |
| 4,692,417 | 9/1987 | Webster | 436/518 |
| 4,784,948 | 11/1988 | Scott et al. | 435/68 |

FOREIGN PATENT DOCUMENTS

| | | |
|---|---|---|
| 0151783 | 12/1984 | European Pat. Off. |
| 8603839 | 12/1985 | WIPO |

OTHER PUBLICATIONS

Maxted, W. R., The Active Agent in Nascent Phage Lysis of Streptococci, *J. Gen. Microbiol.*, vol. 16, 584–595 (1957).
Krause, R. M., Studies on the Bacteriphages of Hemolytic Streptococci, *J. Exp. Med.*, vol. 108, 803–821 (1958).
Barkulis, Chemical and Enzymatic Studies on the Structure and Composition of Group A Streptococcus, Caravano, R., Ed., Excerpta Medica Foundation, 43–50 (1966).
Cohen, J. O. et al, Simple Procedure for Production by Group C Streptococci of Phage-Associated Lysin Active Against Group A Streptococci, *Appl. Microbiol.* vol. 29, 175–178.
McCarty, M., The Lysis of Group A Hemolytic Streptococci by Extracellular Enzymes of Streptomyces Albus, *J. Exp. Med.*, vol. 96, 555–580 (1952).
Bray, J. P. et al., Comparison of Streptomyces Albus Muramidase–Extracted Streptococcal Antigen With Acid–Extracted M Antigen and Pepsin–Extracted T Antigen, *Inf. & Immun.*, vol. 16, 310–317 (1977).
Watson, B. K. et al, Identification of Streptococci: Use of Lysozyme and Streptomyces Albus Filtrate in the Preparation of Extracts for Lancefield Grouping, *J. Clin. Micro.*, vol. 1, 274–278 (1975).
Ederer, G. M. et al, Rapid Extraction Method With Pronase B for Grouping Beta–Hemolytic Streptococci, *Appl. Microbiol.*, vol. 23, 285–288 (1971).
Huang, J. C. et al, Serogrouping of Groups A, B, C, D, F and G Streptococci by Enzyme–Linked Immunosorbent Assay (ELISA), Bureau of Microbiology, Laboratory Centre for Disease Control, Ottawa, Ontario.
Krause, R. M., Antigenic Components of Hemolytic Streptococci, Immunopathology, Third International Symposium, La Jolla, California (1963), Schwabe & Co., Publishers, Basel, Switzerland, 282–289.
Williams & Chase, Methods in Immunology and Immunochemistry, 34–39 (1967).
Kantor, F., et al., *Journ Exp Med*, 112:77–96 (1960).
Phillips, G., et al., *Proc. Natl. Acad. Sci.*, 78 No. 8:4689–4693 (1981).
Nahm, M., et al, *Journ Clin Micro*, 12 No. 4:506–508 (1980).
Fischetti, V., et al., *Journ Exp Med.*, 133 No. 5:1105–1117 (1971).
Cohen, J., et al., *Appl. Microbiol.*, 29 No. 2:175–178 (1975).
McCartly, L., in "Rapid Detection and Identification of Infectious Agents" (Academic Press, Orlando, Florida) Kingsbury & Falkow eds, pp. 165–175 (1985).
V. Fischetti et al, "Size Variation of the M Protein in Group A Strepococci" in *J. Exp. Med* 161 (6):1384–1401 (Jun. 1985).
Okuhara et al, "Preparation of Group A Streptococcal Cell Membrane by Treatment with Group C Streptococcus Phase–Associated Lysin", Annales Paediatrici Japonici 29(2)10–19 Jun. 1983.
Yarnell et al, "Isolation and characterization of a tupe II Fc receptor from a group a streptococus", Molecular and Cellular Biochemistry 70 (1) 57–66, 1986.
Erwa, "Studies On The Two Methods For Extraction Of Streptococcal T Antigens," *J. Hyg.*, 71:131–138 (1973).
Krause, "Studies On The Bacteriophages Of Hemolytic Streptococci. II. Antigens Released From The Streptococcal Cell Wall By A Phage–Associated Lysin," *J. Exp. Med.*, 108:803–821 (1985).

*Primary Examiner*—Carol A. Spiegel
*Attorney, Agent, or Firm*—Foley & Lardner

[57] ABSTRACT

The present invention relates to the rapid detection of Group A streptococci in clinical specimens, through the enzymatic digestion by a semi-purified Group C streptococcal phage associated lysin enzyme and the identification of the released antigens, through the reaction of a labelled ligand and its respective antigen or receptor. The labelled ligand can be included during the digestion of the bacteria, enabling the total assay time to be less than five minutes. The lysin enzyme is stabilized and can be lyophilized for in situ reconstitution.

23 Claims, No Drawings

METHOD FOR EXPOSING GROUP A STREPTOCOCCAL ANTIGENS AND AN IMPROVED DIAGNOSTIC TEST FOR THE IDENTIFICATION OF GROUP A STREPTOCOCCI

This application is a continuation of application Ser. No. 07/919,616, filed Jul. 29, 1992, now abandoned which is a continuation of application Ser. No. 06/916,800, filed Oct. 8, 1986 (now abandoned).

BACKGROUND OF THE INVENTION

Group A streptococci have been shown to be an important pathogen capable of existing both in a carrier state in an asymptomatic individual and in a symptomatic individual with symptoms of disease ranging from a mild sore throat, tonsillitis, or impetigo. If untreated these streptococcal infections could lead to glomerulonephritis, rheumatic fever and possibly permanent rheumatic heart disease. With the advent of antimicrobial agents, specifically penicillin derived antibiotics, the causative organism can be readily eliminated following the prescribed regimen of appropriate antibiotic therapy.

The fact that an infected individual (usually children & young adults) can pass group A streptococcal organisms to others, particularly in daycare centers and schools, necessitates the isolation of the known infected individual away from these environments for at least 24 to 72 hours after antimicrobial therapy has been initiated. It has been shown in controlled studies that early detection and appropriate treatment results in a reduction in the overall pattern of cyclic transmission of the troublesome pathogen as well as a reduction or elimination of the sequelae of group A infections (rheumatic fever or nephritis).

The first individual to identify the serological and immunological groups of streptococci was Dr. Rebecca Lancefield, (Lancefield, R. C., "A Serological Differenitation of Human and other Groups of Hemolytic Streptococci," J. Exp. Med., Vol. 57, pp 571–595 {1933}), after whom the grouping system was named. The group A streptococcus was identified on the basis of B-1, 4 N-acetylglucosamine terminal sugar moieties on a repeating rhamnose sugar backbone found as part of the structure of the organism's cell wall. Antiserum raised against group A streptococci and subsequent absorptions to remove cross-reactions were shown to specifically react with the cell wall component of these organisms and became the grouping antisera for group A streptococci. A number of methods have been devised to fragment the group A streptococcal cell wall carbohydrate. These methods include heating by boiling at pH 2.0, autoclaving, trichloroacetic acid extraction, hot formamide digestion, nitrous acid extraction and enzyme digestion by enzymes derived from the soil microorganisms of species streptomyces, and the phage-associated enzyme lysin. Each of these methods have various advantages and disadvantages.

The rapid diagnosis of group A streptococcal pharyngitis has become more readily available to both physicians and clinical laboratories by replacing time consuming culturing methods requiring a minimum of 24 to 72 hours to identify the presence of group A streptococci with a rapid antigen-antibody test capable of being performed and read in less than one hour. Culturing methods vary in the degree of sensitivity of detection. In one case, a simple 5% sheep blood agar plate may be used in conjunction with a Bacitracin disc and culturing 24 hours at 37° C. aerobically to identify group A streptococci. Alternatively, a selective media and anaerobic conditions may be used to inhibit overgrowth by other organisms and incubation at 35° C. for a minimum of 48 hours. In addition, depending on the transport media, the delay in testing, and any antibacterial agents that the patient may have taken, culturing may result in nonviable organisms that fail to grow in the media although the patient is indeed colonized by the group A streptococcus. In the latter case a sensitive immunoassay for group A streptococcal antigen can detect these nonviable organisms.

The sensitivity of the immunoassay procedure is effected by the amount of group A streptococcal carbohydrate antigen released and recognized by the specific immunological reagent. Enzymatic digestion by enzymes such as that produced by the species streptomyces, have proven to be quite effective in antigen release over some chemical methods and micro-nitrous acid but the poor specific activity and the presence of proteases makes it slow and incompatible for prolonged contact with immunological reagents.

Maxted, (Maxted, W. R., "The Active Agent in Nascent Phage Lysis of Streptococci," J. Gen Micro, vol 16, pp 585–595 {1957}), Krause, (Krause, R. M., "Studies on the Bacteriophages of Hemolytic Streptococci," J. Exp Med, vol 108, pp 803–821 {1958}), and Fischetti, (Fischetti, V. A., et al, "Purification and Physical Properties of Group C Streptococcal Phage Associated Lysin," J. Exp Med, Vol 133 pp 1105–1117 {1971}, have reported the characteristics of an enzyme produced by the group C streptococcal organism after being infected with a particular bacteriophage identified as C1. The enzyme was given the name lysin and was found to specifically cleave the cell wall of group A, group C and group E streptococci. These investigators provided information on the characteristics and activities of this enzyme with regards to lysing the group A streptococci and releasing the cell wall carbohydrate. They never reported on the utility of this enzyme in an immunological diagnostic test for the detection of group A streptococci from throat swabs in patients. The failure to use this enzyme for a clinical diagnostic test was due to a number of problems associated with the enzyme such as: the difficulty in growing large amounts of bacteriophage in the group C streptococci, the time delays in inactivating the residual enzyme when trying to obtain phage stocks, the instability of the enzyme itself to oxidative conditions and heat, and nonspecific reactions in immunoassays performed in the presence of other organisms and the biological components in the sample. We have addressed and solved each of these problems and have incorporated the improvements into the present invention.

The rapid and sensitive detection of group A streptococcal antigens is provided by a diagnostic test kit which utilizes a sampling device consisting of a throat swab made of synthetic or natural fibers such as dacron or rayon and some type of shaft which holds the fibers and which is long enough to place the fibers in the tonsillar area and capable of being used to swab the area to remove sufficient numbers of colonizing or infecting organisms. The swab can then be placed in the enzyme extraction reagent in several configurations and subsequently used in an immunoassay.

SUMMARY OF THE INVENTION

The ability to identify the presence of Group A Streptococci in a biological sample, such as a throat swab, saliva, or an infected lesion is rapid and reliable when using the methods identified in the present invention. An applicator swab is used to transfer the organisms from an infected area to an assay solution. The swab containing the infecting organisms is placed in a solution containing the Group C Streptococcal phage lysin enzyme (Lysin) which will digest the cell wall of any Group A Streptococci present in the swab, releasing the Group A carbohydrate as well as other cell wall antigens in solution. The incubation time for this procedure is rapid, generally 1–4 minutes.

The invention can comprise a test kit for detecting Group A streptococcus, comprising an extraction reagent containing lysin enzyme for releasing Group A streptococcal components, and a ligand capable of binding with a component of the Group A streptococcus.

The present invention is based upon the discovery that phage lysin can effectively and efficiently breakdown the cell wall of Group A Streptococci and the resultant antigenic fragments are reactive with antibodies specific for the Group A Streptococcal carbohydrate and that when such antibodies are labelled with a particle, flourescent or non flourescent, chromophore, or an enzyme, the resultant antibody complex can be detected in an appropriate immunoassay. The semi-purified enzyme is lacking in proteolytic enzymatic activity and therefore non destructive to specific antibodies when present during the digestion of the bacterial cell wall and therefore more effective in reducing assay time when the labelled antibody and enzyme are used in combination. It will be apparent to those skilled in the art that phage lysin can be advantageously used in many different types of assays known in the art which are designed for the diagnosis of Streptococcal Group A infection, for example ligand receptor assay, agglutination assays, enzyme linked immunoassays, fluorescent immunosassays, and chromophore linked immunoassays.

DETAILED DESCRIPTION OF THE INVENTION

Described herein is an improved method of extraction and a diagnostic test for the identification of group A streptococci from infected tissues. The test may be performed in a single step and provides the user with an answer in less than 5 minutes without the need for complicated equipment or experience. This permits the test to be performed in both the doctor's office as well as the home. Thus, the doctor is able to determine the course of treatment rapidly without the need to delay 24 to 48 hours for the results of conventional assays. The assay depends on the rapid and efficient extraction of antigen from the streptococcus in the specimen rather than waiting for the organisms to grow on culture media for identification. The activity of the extracting enzyme and the specificity of the antibody probe allow the invention assay to be nearly as accurate and as sensitive as the conventional culture test.

In accordance with the present invention, a test kit will be provided for the accurate and rapid identification of group A streptococci from biological specimens. The specimen is collected onto an applicator stick fitted at one end with a fiber swab. The infected area is swabbed to transfer the organisms from the infected tissue to the swab. The swab is then transferred to a solution containing the lysin enzyme in a buffered solution. The contact time between the swab and lysin enzyme is less than 30 minutes and preferably less than 6 minutes. The assay can be performed at room temperatures (21° C. to 29° C.). The enzyme digests the cell wall of any group A streptococci present in the swab and releases the group carbohydrate in solution. An important feature of the invention is the fact that the organisms trapped in the matrix of the fibers will also be digested thus, the organisms do not need to be released in solution for the digestion to occur. Since the enzyme solution exhibits no proteolytic activity, the indicator reagent (antibody specific for the group carbohydrate) may be present in the extracting solution during the extraction process. As antigen is released from a swab containing group A streptococci, the antibody will react with the antigen. Another feature of the invention is the high activity of this enzyme for the group A streptococcal cell wall allowing for complete release of the cell wall antigen in less than 5 minutes.

EXAMPLE 1

The extraction reagent containing the group C phage lysin enzyme is prepared as follows:

Group C streptococcal strain 26RP66 (ATCC #21597) or any other group C streptococcal strain is grown in Todd Hewitt medium at 37° C. to an OD of 0.23 at 650 nm in an 18 mm tube. Group C bacteriophage (C1) (ATCC #21597-B1) at a titer of $5 \times 10^6$ is added at a ratio of 1 part phage to 4 parts cells. The mixture is allowed to remain at 37° C. for 18 min at which time the infected cells are poured over ice cubes to reduce the temperature of the solution to below 15° C. The infected cells are then harvested in a refrigerated centrifuge and suspended in 1/300th of the original volume in 0.1M phosphate buffer, pH 6.1 containing $5 \times 10^{-3}$M dithiotreitol and 10 ug of DNAase. The cells will lyse releasing phage and the lysin enzyme. After centrifugation at 100,000× g for 5 hrs to remove most of the cell debris and phage, the enzyme solution is aliquoted and tested for its ability to lyse Group A Streptococci.

The number of units/ml in a lot of enzyme is determined to be the reciprocal of the highest dilution of enzyme required to reduce the OD650 of a suspension of group A streptococci at an OD of 0.3 to 0.15 in 15 minutes. In a typical preparation of enzyme $4 \times 10^5$ to $4 \times 10^6$ units are produced in a single 12 liter batch.

Use of the enzyme in an immunodiagnostic assay requires a minimum number of units of lysin enzyme per test depending on the incubation times required. The enzyme is diluted in a stabilizing buffer containing the appropriate conditions for stability, maximum enzymatic activity, inhibitors of nonspecific reactions, and in some configurations contains specific antibodies to the Group A carbohydrate. The preferred embodiment is to use a lyophilized reagent which can be reconstituted with water. The stabilizing buffer can comprise a reducing reagent, which can be dithiothreitol in a concentration from 0.001M to 1.0M, preferably 0.005M. The stabilizing buffer can comprise a metal chelating reagent, which can be ethylenediaminetetraacetic acid disodium salt in a concentration from 0.00001M to 1.0M, preferably 0.005M. The stabilizing buffer can comprise an immunoglobulin or immunoglobulin fragments in a concentration of 0.001 percent to 10 percent, preferably 0.1 percent. The stabilizing buffer can comprise a citrate-phosphate buffer in a concentration from 0.001M to 1.0M, preferably 0.05M. The stabilizing buffer can have a pH value in the range from 5.0 to 9.0, preferably 6.1. The stabilizing buffer can comprise a bactericidal or bacteriostatic reagent as a preservative. Such preservative can be sodium azide in a concentration from 0.001 percent to 0.1 percent, preferably 0.02 percent.

The preparation of phage stocks for lysin production is the same procedure described above for the infection of phage and group C streptococcus in the preparation of the lysin enzyme. However, instead of pouring the infected cells over ice, the incubation at 37° C. is continued for a total of 1 hour to allow lysis and release of the phage and also enzyme in the total volume. In order for the phage to be used for subsequent lysin production the residual enzyme must be inactivated or removed to prevent lysis from without of the group C cells rather than phage infection.

In accordance with the current invention, the presence of the group A streptococcal antigen in the extracting reagent is detected by an antigen-antibody reaction (immunoassay) wherein the antibody is labelled with an indicator particle or molecule.

In accordance with the current invention, the ideal embodiment for the detection of the Group A Streptococcal antigen is a chromophore labelled membrane spot test.

It should be understood that the identification of the group A antigen released by the lysin enzyme is not limited to the identification method outlined above. The detection method may be substituted by any immune detection system such as antibody—bound latex particles, radioimmunoassay, immunofluorescence techniques, enzyme linked immunosorbant assay (ELISA) etc.

It should also be understood that the antigen to be detected is not limited to the group A carbohydrate. Since other cell wall antigens are released during the digestion process (i.e. M Protein) antibody detection of these antigens may also be used in the identification of the group A streptococcus.

According to the invention, the test kit will utilize suitable applicator swabs for specimen transfer. The enzyme-containing extraction reagent will be provided in lyophilized form for on-site reconstitution. After reconstitution, the extraction reagent may be maintained at refrigerator temperature (2°–10° C.) for greater than 5 weeks.

EXAMPLE 2

The enzyme prepared according to example 1 is diluted to a concentration of 100 units/ml in a buffer consisting of 0.05M citrate phosphate buffer pH 6.1 containing 0.1% rabbit immunoglobulin, 0.005M (ethylenedinitrilo) tetraacetic acid disodium salt (EDTA), 0.005M Dithiothreitol, 0.02% sodium azide, 0.01% Nacetylglucosamine. One part colloidal gold sol labelled with Group A Streptococcal Antibody ($OD^{520}$ 1.5) suspended in 0.02M Tris buffer pH 8.2, 1.0% bovine serum albumin, 0.02% sodium azide, 300K units heparin, is added to 3 parts of the enzyme reagent, mixed, filtered through a 0.22 micron filter, and 200 microliters aliquoted per tube and lyophilized. This lyophilized reagent is stable at elevated temperatures (i.e. 45° C.) for short term conditions (i.e. 2 weeks) and long term storage at room temperatures (>1 year). A rayon or dacron swab, preferably dry, is used to swab the suspected infected area. Two hundred microliters of deionized water is added to a reaction tube containing the lyophilized chromophore—enzyme mixture and the swab is added and twirled to mix the reagents. After a 4 minute incubation at room temperature, the swab is placed on a device consisting of a 1.2 micron cellulose acetate filter which is situated on top of a plastic laminate containing 2 holes, that are each 1.5 mm in diameter. Below one well is fixed a detection membrane saturated with rabbit anti Streptococcal Group A capture antibody and under the other a control membrane saturated with rabbit non-immune immunoglobulin. Both membranes are situated on top of an absorbant paper to draw any excess fluid from the swab thru the membranes. If Group A Antigen is present, the immune complex is deposited and captured on the detection membrane and a pink to black color can be visualized on the detection membrane. In the absence of Group A Streptococcal Antigen the chromophore labelled antibody diffuses through the membrane and is not visible on that membrane. Using swabs seeded with Group A Streptococci it is possible to detect $2\times10^4$ organisms in less than five minutes. The addition of heparin, 0.01% N-acetyl glucosamine, 0.1% rabbit immunoglobulin and a 1–2 micron filter overlay are necessary to reduce the occurence of nonspecific reactions encountered in clinical throat specimens.

In another embodiment for the detection of group A streptococci, the lysin extraction reagent is typically provided in lyophilized form for on site reconstitution. Before reconstitution the extraction reagent may be stored refrigerated (2° to 8° C.) for at least 30 days without any significant loss of enzyme activity. Reconstituted extraction reagent is dispensed (typically 200 microliters). The throat swab is placed in the sample cup and incubated for at least 2 minutes at room temperature to allow the enzyme to free the strepococcal cell wall antigens from the swab fibers. After the incubation period, the swab is rotated and squeezed against the wall of the sample cup to express the fluid. An aliquot of the fluid can then be tested in an immunoassay, such as latex agglutination.

EXAMPLE 3

A commercial latex agglutination assay kit for the direct detection of group A streptococci (Streptogen, New Horizons Diagnostics) was utilized to examine the suitability of the lysin extraction reagent with latex agglutination reagents. Swab's were seeded with known concentrations of group A streptococci and then incubated over 2 to 10 minutes at room temperature in an extraction reagent containing various concentrations of lysin.

One drop (approximately 40 microliters) of the expressed fluid was applied to both a detection and control circles on a glass plate. One drop of detection latex (rabbit anti Group A antibody coated latex) was added to the detection circle and one drop of control latex (rabbit nonimmune gamma globulin coated latex) was added to the control circle. The reactants were rotated on a mechanical rotator for 2 minutes and the detection and control circles were examined for the presence of agglutination. The results of this experiment is summarized in Table I.

TABLE I

The effect of incubation time and lysin concentration on the sensitivity of detection of group A *streptococci* by a latex agglutination assay.

| Units of lysin /ml | Incubation time Minutes | Least Number of Organisms Detected |
|---|---|---|
| 30 | 2 | $1.5 \times 10^3$ |
| 30 | 3 | $7.5 \times 10^4$ |
| 30 | 4 | $1.8 \times 10^4$ |
| 30 | 5 | $9 \times 10^3$ |
| 30 | 10 | $9 \times 10^3$ |
| 120 | 2 | $1.8 \times 10^4$ |
| 120 | 3 | $9 \times 10^3$ |
| 120 | 4 | $9 \times 10^3$ |
| 120 | 5 | $9 \times 10^3$ |
| 120 | 10 | $9 \times 10^3$ |

The results indicate that the release of group A carbohydrate by lysin enzyme is dependent upon lysin concentration and incubation time.

Clinical throat swab specimens were cultured on 5% sheep blood agar plate and the swab was then tested by a latex agglutination assay using a 3 minute room temperature (25° C.) lysin extraction (20 units lysin per test) incubation. A summary of the results are as follows:

|  | Latex Positive | Latex Negative |
|---|---|---|
| Culture Positive | 10 | 0 |
| Culture Negative | 1 | 55 |

Various modifications of this invention as specifically described herein will be apparent to those skilled in the art. All such modifications are intended to be within the spirit and scope of this invention, which is limited solely as defined in the following claims:

What is claimed is:

1. A method for detecting Group A streptococcal antigens, comprising:

treating a clinical specimen suspected of containing Group A streptocooci with an extraction reagent comprising Group C streptococcal phage associated lysin enzyme without first culturing said clinical specimen thereby releasing Group A streptococcal antigens into the extraction reagent and detecting said antigens using an immunological ligand receptor assay, wherein the contact time between the clinical specimen and said extraction reagent is less than six minutes and wherein all procedures of the assay are performed at room temperature from 21° C. to 29° C., and wherein said lysin enzyme lacks proteolytic activity with respect to antibody specific to Group A streptococcal antigen.

2. The method of claim 1, wherein the clinical specimen is collected from a collection site utilizing a natural or synthetic fiber swab attached to one end of an applicator stick.

3. The method of claim 1, wherein the ligand receptor assay is an immunoassay selected from the group consisting of agglutination, enzyme-linked, fluorescent and chromophore-linked immunoassays.

4. The method of claim 1, wherein the immunoassay comprises a specific antibody which is covalently attached or passively adsorbed to an indicator particle, indicator molecule, or a detection membrane.

5. The method of claim 4, wherein the clinical specimen is placed in a solution comprising the specific antibody and said extraction reagent.

6. The method of claim 1, wherein a Group A carbohydrate cell wall antigen is released.

7. The method of claim 1, wherein an M protein antigen is released.

8. The method of claim 1, wherein said extraction free agent comprises a stabilizing buffer to allow optimum activity of said lysin enzyme.

9. The method of claim 8, wherein the stabilizing buffer comprises a reducing reagent.

10. The method of claim 9, wherein the reducing reagent is dithiothreitol.

11. The method of claim 1, wherein said extraction reagent is a lyophilized reagent which is reconstituted with liquid prior to performing the assay.

12. The method of claim 8, wherein the stabilizing buffer comprises a metal chelating reagent.

13. The method of claim 12, wherein the metal chelating reagent is ethylenediaminetetraacetic acid disodium salt.

14. The method of claim 8, wherein the stabilizing buffer comprises immunoglobulin or immunoglobulin fragments.

15. The method of claim 8, wherein the stabilizing buffer comprises a citrate-phosphate buffer.

16. The method of claim 8, wherein the stabilizing buffer has a pH value in the range from 5.0 to 9.0.

17. The method of claim 8, wherein the stabilizing buffer comprises a bactericidal or bacteriostatic reagent as a preservative.

18. The method of claim 17, wherein the preservative is sodium azide.

19. A diagnostic kit for detecting Group A streptococcus in clinical specimens, comprising:

an extraction reagent containing streptococcal Group C phage-associated lysin enzyme for releasing Group A streptococcal antigens, wherein said lysin enzyme lacks proteolytic activity with respect to antibody specific to Group A streptococcal antigen, and an immunological ligand which binds with one or more of said Group A streptococcal antigens.

20. The test kit according to claim 19, wherein the extraction reagent is provided as a lyophilized reagent.

21. The test kit according to claim 19, wherein the ligand which binds with said one or more of said Group A streptococcal antigens is a labelled antibody comprising a specific antibody which is covalently attached or passively adsorbed to an indicator particle, an indicator molecule or a detection membrane.

22. A diagnostic enzymatic extraction assay for Group A streptococcus, in which a clinical specimen suspected of containing Group A streptococcus is treated with an enzymatic extraction reagent to release Group A streptococcal antigen present in said clinical specimen, and in which the presence or absence of said antigen is determined using immunological reagents which bind to said antigen, the improvement comprising:

treating said clinical specimen with an extraction reagent comprising streptococcal Group C phage associated lysin enzyme to release said Group A streptococcal antigen into said extraction reagent, wherein said lysin enzyme lacks proteolytic activity with respect to antibody specific to Group A streptococcal antigen.

23. A method for detecting Group A streptococcal antigens, comprising the steps of:

preparing a single reagent comprising Group C streptococcal phage associated lysin enzyme and an antibody or antibody fragment specific to said Group A streptococcal antigens, wherein said lysin enzyme lacks proteolytic activity with respect to antibody specific to Group A streptococcal antigen, treating a clinical specimen suspected of containing Group A streptococci with said single reagent thereby releasing Group A streptococci antigens from said clinical specimen into said reagent, and immunologically detecting said released Group A streptococcal antigens.

\* \* \* \* \*